(12) United States Patent
Austin et al.

(10) Patent No.: US 6,945,994 B2
(45) Date of Patent: Sep. 20, 2005

(54) COMBINED BALLOON-EXPANDING AND SELF-EXPANDING STENT

(75) Inventors: Michael John Stephen Austin, Tuam (IE); Barry O'Brien, Barna (IE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 09/683,249

(22) Filed: Dec. 5, 2001

(65) Prior Publication Data
US 2003/0105516 A1 Jun. 5, 2003

(51) Int. Cl.$^7$ ................................................ A61F 2/06
(52) U.S. Cl. ..................... 623/1.16; 623/1.15; 623/1.2; 623/23.7
(58) Field of Search ................ 623/1.1–1.2, 1.15, 623/1.16, 23.7; 606/108, 191, 194, 198

(56) References Cited

U.S. PATENT DOCUMENTS

| | | | |
|---|---|---|---|
| 5,091,205 A | 2/1992 | Fan | 427/2 |
| 5,383,892 A * | 1/1995 | Cardon et al. | 623/1.16 |
| 5,601,593 A * | 2/1997 | Freitag | 623/1.19 |
| 5,807,404 A | 9/1998 | Richter | 623/1 |
| 5,843,120 A | 12/1998 | Israel et al. | 606/198 |
| 5,843,172 A | 12/1998 | Yan | 623/1 |
| 5,972,027 A | 10/1999 | Johnson | 623/1 |
| 6,096,070 A * | 8/2000 | Ragheb et al. | 623/1.39 |
| 6,168,621 B1 | 1/2001 | Vrba | 623/1.2 |
| 6,264,687 B1 * | 7/2001 | Tomonto | 623/1.16 |
| 6,315,708 B1 | 11/2001 | Salmon et al. | 600/3 |
| 6,336,937 B1 * | 1/2002 | Vonesh et al. | 623/1.13 |
| 6,409,750 B1 * | 6/2002 | Hyodoh et al. | 623/1.1 |
| 6,451,052 B1 | 9/2002 | Burmeister et al. | 623/1.16 |
| 6,485,507 B1 | 11/2002 | Walak et al. | 623/1.15 |
| 6,488,702 B1 * | 12/2002 | Besselink | 623/1.15 |
| 6,582,461 B1 | 6/2003 | Burmeister et al. | 623/1.18 |
| 2003/0208263 A1 | 11/2003 | Burmeister et al. | 623/1.19 |

FOREIGN PATENT DOCUMENTS

| | | |
|---|---|---|
| WO | 95/31945 | 11/1995 |
| WO | 96/26689 | 9/1996 |
| WO | 00/33770 | 6/2000 |
| WO | 01/08600 | 2/2001 |
| WO | 01/35864 | 5/2001 |

OTHER PUBLICATIONS

U.S. Appl. No. 09/702,226, filed Oct. 31, 2000, Walak.
U.S. Appl. No. 09/427,291, filed Oct. 26, 1999, Burmeister et al.
"Shape Memory Stainless Steels," Zhao, Chenxu, *Advanced Materials & Processes*, pp. 33–35 (Feb. 2001).

* cited by examiner

*Primary Examiner*—Michael Thaler
(74) *Attorney, Agent, or Firm*—Vidas, Arrett & Steinkraus

(57) ABSTRACT

A stent comprises a plurality of segments including a first balloon expandable segment which is not self-expanding, a second balloon expandable segment which is not self-expanding and a first self-expanding segment. The first self-expanding segment is disposed between the first and second balloon expandable segments. The segments are axially displaced from one another.

9 Claims, 3 Drawing Sheets

COMBINED BALLOON-EXPANDING AND SELF-EXPANDING STENT

BACKGROUND OF INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in other bodily vessels including arteries, veins, biliary ducts, urethras, fallopian tubes, bronchial tubes, the trachea and the esophagus.

Stents are typically either self-expanding or mechanically expandable via the application of radially outward force from within the stent, as by inflation of a balloon. An example of a balloon expandable stent is shown in U.S. Pat. No. 5,843,120. An example of a self-expanding stent is described in WO 96/26689. Hybrid stents, e.g. stents which are both self-expanding and mechanically expandable are also known. Examples of hybrid stents are disclosed in U.S. Pat. No. 6,168,621 and WO 01/08600.

The use of coatings which contain active pharmacological agents or drugs for therapeutic uses such as inhibiting restenosis is known in the art. While the use of therapeutic coatings holds enormous promise, one limitation that occurs with coatings arises due to the work hardening nature of the stainless steel that is typically found in many stents. After deployment of the stent and after the therapeutic coating has had an effect on the vessel in which the stent is implanted, there is a possibility that the stent may lose its initial tight fit in the vessel which could result in migration of the stent.

There remains a need for a stent which provides some of the benefits of balloon expandable stents and self-expanding stents and which, in particular, when provided with a therapeutic coating, will maintain a tight fit in a vessel even after the coating has had an effect on the vessel.

All U.S. patents and all other published documents mentioned anywhere in this application are incorporated herein by reference in their entirety.

Without limiting the scope of the invention, a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

SUMMARY OF INVENTION

In one embodiment, the invention is directed to a stent comprising a plurality of segments including a first balloon expandable segment which is not self-expanding, a second balloon expandable segment which is not self-expanding and a first self-expanding segment. The first self-expanding segment is disposed between the first and second balloon expandable segments. The segments are axially displaced from one another.

Typically, the stent further comprises a second self-expanding segment which is disposed between the first and second balloon expandable but not self-expanding segments. Optionally, the stent may further comprise a third balloon expandable segment with the second self-expanding segment disposed between the second balloon expandable segment and the third balloon expandable segment.

The invention is also directed to a stent having first and second ends which are not self-expanding and one or more self-expanding segments therebetween.

The invention is further directed to a stent comprising a plurality of interconnected cells, some of the cells being self-expanding and some of the cells being balloon expandable but non-self-expanding. The self-expanding cells are provided in one or more islands amongst the balloon expandable but non-self-expanding cells. At least one of the islands is either an end island located at an end of the stent or an intermediate island located between ends of the stent. The end island extends over less than the entire circumference of the stent and is circumferentially and axially adjacent to balloon expandable but non-self-expanding cells. The intermediate island is surrounded by balloon expandable but non-self-expanding cells.

Typically, the stent will comprise a plurality of islands of self-expanding cells. Desirably, the islands are regularly distributed about the stent. Also typically, the stent will comprise more balloon expandable but non-self-expanding cells than self-expanding cells. Desirably, each of the islands contains more than one self-expanding cell.

The invention is also directed to a stent comprising a plurality of sections including at least one self-expanding section which extends helically about the stent and at least one balloon expandable but non-self-expanding section which extends helically about the stent. Typically, the stent will comprise a plurality of the self-expanding sections and a plurality of the balloon expandable but non-self-expanding sections. Desirably, the self-expanding sections and the balloon expandable but non-self-expanding sections alternate with one another along the length of the stent. More desirably, the balloon expandable but non-self-expanding sections are of the same width as the self-expanding sections. The balloon expandable but non-self-expanding sections are optionally wider than the self-expanding sections. In one embodiment, the balloon expandable but non-self-expanding sections are twice the width as the self-expanding sections.

In accordance with the invention, each of the sections optionally may be stepped. Also in accordance with the invention, each of the sections optionally may comprise a plurality of cells. Further in accordance with the invention, each of the sections optionally may be in the form of a serpentine band.

The invention is further directed to a stent comprising a plurality of sections including at least one self-expanding section which extends in one direction about a longitudinal axis of the stent and at least one balloon expandable but non-self-expanding section which extends in another direction about the longitudinal axis of the stent. Typically, the stent will comprise a plurality of self-expanding sections and a plurality of balloon expandable but non-self-expanding sections. Optionally, the self-expanding section or sections may extend in a first helical direction and the balloon expandable but non-self-expanding section or sections may extend in a second helical direction.

The invention is also directed to a method of manufacturing a stent comprising the steps of providing a tubular stent preform or a stent preform in the form of a sheet where the stent preform is made of a non-self-expanding material having a plurality of first openings therein corresponding to a desired stent pattern and at least one second opening therein for receiving a self-expandable stent material therein and disposing a self-expandable segment in the second opening and securing it to the stent preform. Where the stent preform is in the form of a sheet, the method further comprises the steps of rolling the sheet to form a tube. Typically, the stent preform has a plurality of second openings therein and a self-expandable segment is disposed in each second opening and secured to the stent preform.

In accordance with the invention, the stent preform may be made of stainless steel and the self-expandable segments are made of a shape memory alloy. Other suitable materials may also be used for the stent preform and for the self-expandable segments. Desirably, the shape memory alloy is a stainless steel shape memory alloy. One suitable stainless steel shape memory alloy for use in the inventive stents is an FeMnSiCrNi shape memory stainless steel.

Any suitable technique may be used to secure the self-expandable segments to the stent preform including via laser welding.

The invention is further directed to a method of manufacturing a stent comprising the steps of providing a stent preform in the form of a tube or a sheet, the stent preform made of a first metal and a second metal secured one to the other, rolling the sheet into a tube where the stent preform is in the form of a sheet, optionally welding the tubular rolled sheet, polishing the tube, disposing an anti-galvanic coating on the tube and disposing a paclitaxel/SIBS (styrene isobutylene styrene) compound on the anti-galvanic coating.

The invention is also directed to a stent with a biological treatment coating disposed thereon. The stent comprises at least one balloon expandable non-self-expanding section and at least one self-expanding section.

The invention is further directed to a method of manufacturing a stent comprising the steps of disposing a tube on a mandrel, the tube comprising at least one section which is self-expanding and at least one section which is balloon expandable but non-self-expanding and heat treating the tube with the at least one self-expanding section expanded to a cross-section at least in excess, and desirably at least 10% in excess, of the maximum diameter of the balloon expandable but non-self-expanding section.

The invention is also directed to a stent comprising an FeMnSiCrNi shape memory stainless steel. Desirably, the stent further comprises a balloon expandable non-shape memory metal. Optionally, the entirety of the stent may be made of the FeMnSiCrNi shape memory stainless steel.

The invention is also directed to a method of manufacturing a stent comprising the steps of providing a stent preform in the form of a tube or a sheet, the stent preform made of a first metal and a second metal secured one to the other, the first metal being a shape memory metal, the second metal being a non-shape memory metal, providing a plurality of openings in the first metal and providing a plurality of openings in the second metal and, where the stent preform is in the form of a sheet, rolling the sheet into a tube.

Additional details and/or embodiments of the invention are discussed below.

DETAILED DESCRIPTION

Figure 1A:
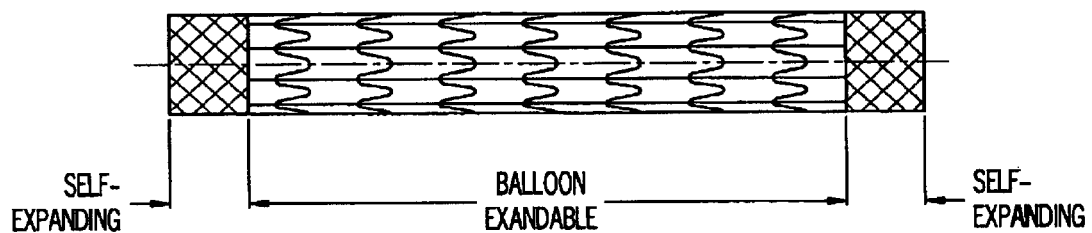
FIG. 1 shows a schematic illustration of an inventive stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1B:
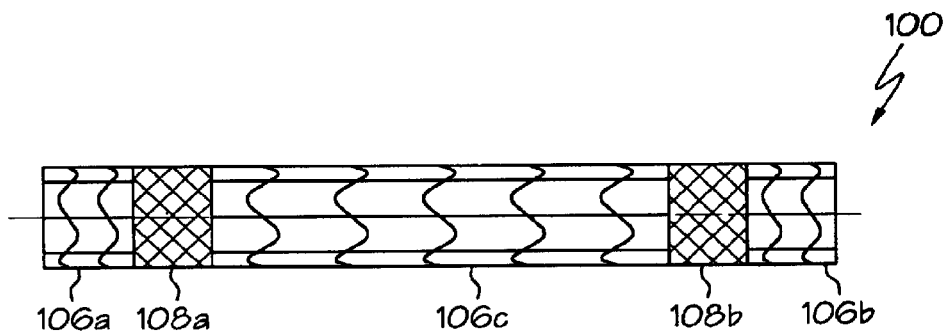

In one embodiment, the invention is directed to a stent such as that shown generally at 100 in FIG. 1, comprising a plurality of segments including a first balloon expandable segment 106a which is not self-expanding, a second balloon expandable segment 106b which is not self-expanding and a first self-expanding segment 108a. The first self-expanding segment 108a is disposed between the first and second balloon expandable segments 106a and 106b. The segments are axially displaced from one another.

Typically, as shown in FIG. 1, the stent further comprises a second self-expanding segment 108b which is disposed between the first and second balloon expandable but not self-expanding segments 106a and 106b. Optionally, the stent may further comprise a third balloon expandable segment 106c with the second self-expanding segment 108b disposed between the second balloon expandable segment 106b and the third balloon expandable segment 106c.

The cellular design of the balloon expandable segments of the embodiment of FIG. 1 is meant to be illustrative but not limiting. Any other cellular design may be used in the balloon expandable but not self-expanding segments. The invention also contemplates using different cellular designs in one or more of the balloon expandable segments of the stent. The cells may be of the open cell design or of the closed cell design, as known in the art.

Similarly, the cellular design of the self-expanding segments of the embodiment of FIG. 1 is meant to be illustrative but not limiting. Any other cellular design may be used in the self-expanding segments. The invention also contemplates using different cellular designs in one or more of the self-expanding segments of the stent.

To that end, the invention is also directed to a hybrid stent having three or more segments including one or more balloon expandable but not self-expanding segments and one or more self-expanding segments where at least one of the balloon expandable but not self-expanding segments has a different cellular structure from other balloon expandable but not self-expanding segments and/or where at least one of the self-expanding segments has a different cellular structure from other self-expanding segments.

The invention is also directed to a stent, such as that shown by way of example in FIG. 1, having first and second ends which are not self-expanding and one or more self-expanding segments therebetween.

Figure 2:
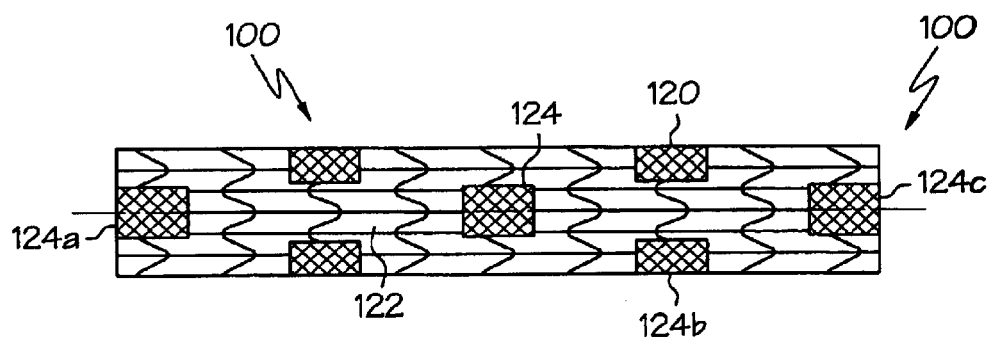
FIG. 2 shows a schematic illustration of another inventive stent.

The invention is further directed to a stent, such as that shown generally at 100 in FIG. 2, comprising a plurality of interconnected cells. Some of the cells are self-expanding 120 and some of the cells are balloon expandable but non-self-expanding 122. The self-expanding cells are provided in one or more islands 124 amongst the balloon expandable but non-self-expanding cells 122. At least one of islands 124 is either an end island 124a located at an end of the stent or an intermediate island 124b located between ends of the stent. The end island extends over less than the entire circumference of the stent and is circumferentially and axially adjacent to balloon expandable but non-self-expanding cells. The intermediate island is surrounded by balloon expandable but non-self-expanding cells.

Typically, the stent will comprise a plurality of islands of self-expanding cells. Also typically, as shown in FIG. 2, one or more of the islands do not extend entirely about the circumference of the stent. Desirably, as shown in FIG. 2, the islands are regularly distributed about the stent. Also typically, the stent will comprise more balloon expandable but non-self-expanding cells than self-expanding cells. Desirably, each of the islands contains at least one self-expanding cell. More desirably, one or more of the islands contains a plurality of cells. Typically, one or more of the islands will contains anywhere from one cell to four cells. As the ratio of stent diameter to cell size increases, the number of cells which can be accommodated per island increases.

In one desirable embodiment, at least two self-expanding cells are provided in each circumferential region of the stent. In another desirable embodiment, the self-expanding cells are not provided in every circumferential region of the stent, but those circumferential regions which include self-expanding cells, include at least two islands of self-expanding cells per circumferential region. In yet another desirable embodiment, those circumferential regions which include self-expanding cells, include only one island of self-expanding cells per circumferential region. In yet another desirable embodiment, a plurality of axially aligned islands are provided. In the embodiment of FIG. 2, for example, the islands labeled 124, 124a and 124c are axially aligned with one another. The invention also contemplates embodiments in which two, four, five or more islands are axially aligned with one another. Moreover, it is within the scope of the invention for an inventive stent to have two or more columns of islands with the islands within a column axially aligned with one another.

The cellular structure of all of the balloon expandable but non-self-expanding regions of the stent may be identical or different. Similarly, the cellular structure of the various islands may be the same or one or more islands may have a different cell structure.

The islands may be provided in any shape, regular or irregular. Desirably, the islands will be substantially square, substantially rectangular, substantially diamond, or substantially circular islands of self-expanding metal. In using the term 'substantially' it is noted that the actual shape of the stent islands may deviate from square, rectangular, diamond or circular as a result of the cellular structure of the stent as well as a result of the tubular nature of the stent. The islands may also be of other shapes as well including regular shapes and irregular shapes. Desirably, the islands mate with the adjacent stent structure.

Desirably, at least 50% of the stent is made from one piece balloon expandable stainless steel or other suitable metal. More desirably, at least 80% of the stent is made from one piece of balloon expandable stainless steel or other suitable metal.

It is noted that, size for size, the balloon expanded stent cell structure will create a higher base value radial stiffness than that of an equivalent size of self-expanding stent. Because the islands of self-expanding cells are adjacent to, and attached to the larger area of more rigid balloon-expanded segments, the edges of the self-expanding cells are mounted on a structure with a higher radial expansion force than that produced by the self-expanding cells acting alone. The balloon expanding metal thus acts as a support or foundation for the self-expanding cells.

Figure 3:
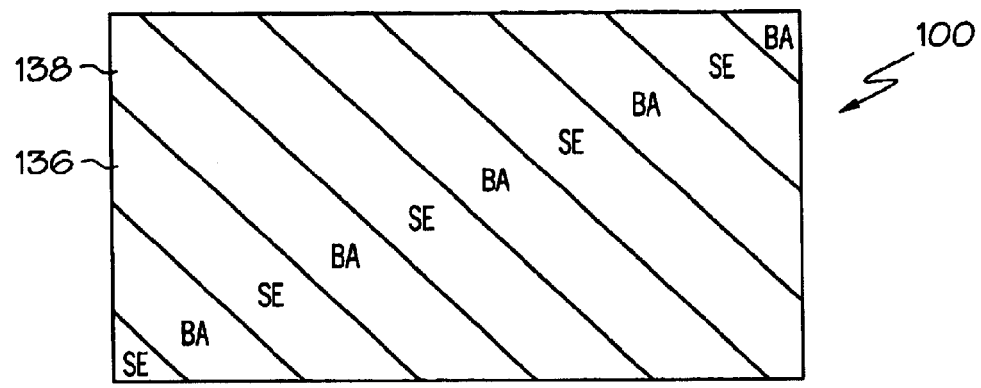
FIG. 3 shows a schematic illustration of yet another inventive stent in side elevational view having strips of self-expanding material and strips of balloon expandable but non-self-expanding material.

The invention is also directed to a stent comprising a plurality of sections, such as that shown generally in side elevational view at 100 in FIG. 3, including at least one self-expanding section 136 (designated in FIG. 3 as SE) which extends helically about the stent and at least one balloon expandable but non-self-expanding section 138 (designated as BA in FIG. 3) which extends helically about the stent. Typically, the stent will comprise a plurality of the self-expanding sections 136 and a plurality of the balloon expandable but non-self-expanding sections 138. Desirably, as shown in FIG. 3, the self-expanding sections and the balloon expandable but non-self-expanding sections alternate with one another along the length of the stent. More desirably, the balloon expandable but non-self-expanding sections are of the same width as the self-expanding sections. Optionally, as shown in side elevational view in FIG. 4, the balloon expandable but non-self-expanding sections may be wider than the self-expanding sections. For example, in the embodiment of FIG. 4, the balloon expandable but non-self-expanding sections are twice the width as the self-expanding sections. It is also within the scope of the invention for the self-expanding and balloon expandable but non-self-expanding sections to be provided in an irregular arrangement or in a non-alternating arrangement.

Figure 5:
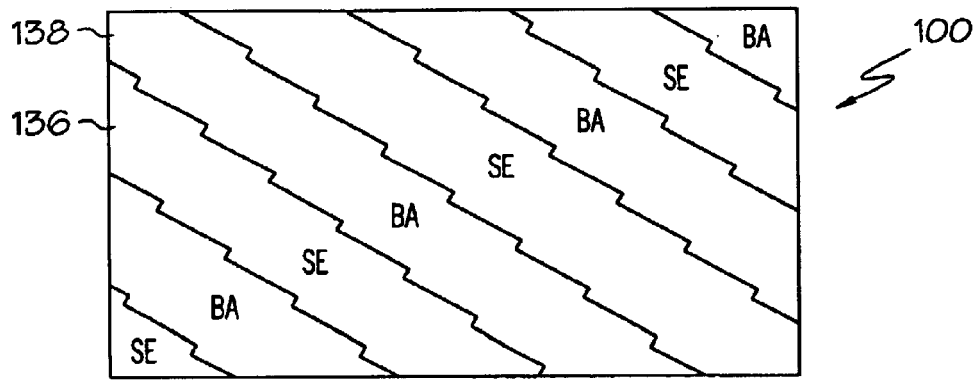
FIG. 5 shows yet another schematic illustration of an inventive stent in side elevational view having strips of self-expanding material and strips of balloon expandable but non-self-expanding material.

In accordance with the invention, as shown in side elevational view in FIG. 5 by way of example only, at least some and desirably, each of the balloon expandable but non-self-expanding sections and each of the self-expanding sections optionally may be stepped. Also in accordance with the invention, each of the sections optionally may comprise a plurality of cells. Further in accordance with the invention, each of the sections optionally may be in the form of a serpentine band.

Figure 4:
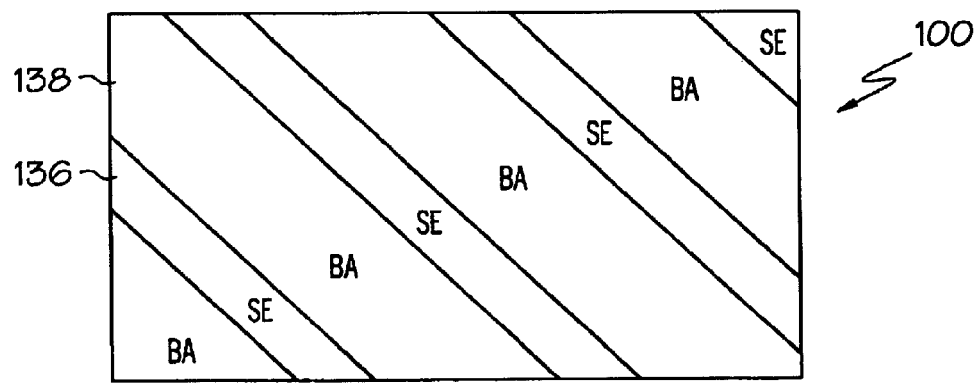
FIG. 4 shows a schematic illustration of yet another inventive stent in side elevational view having strips of self-expanding material and strips of balloon expandable but non-self-expanding material where the strips are of different widths.

Desirably, in the embodiments of FIGS. 3–5, the self-expanding sections are of cellular design and the balloon expandable but non-self-expanding segments are of cellular design as well. Each of the sections may be of the same cellular design or may be of different cellular design. For example, the balloon expandable but non-self-expanding sections may be of different cellular design from the self-expanding sections. It is also within the scope of the invention for some of the balloon expandable but non-self-expanding sections to have one cellular design and for other balloon expandable but non-self-expanding sections to be of another cellular design and likewise for the self-expanding segments. The balloon expandable but non-self-expanding sections and the self-expanding sections may also be in the form of serpentine sections which do not define cells.

Figure 6A:
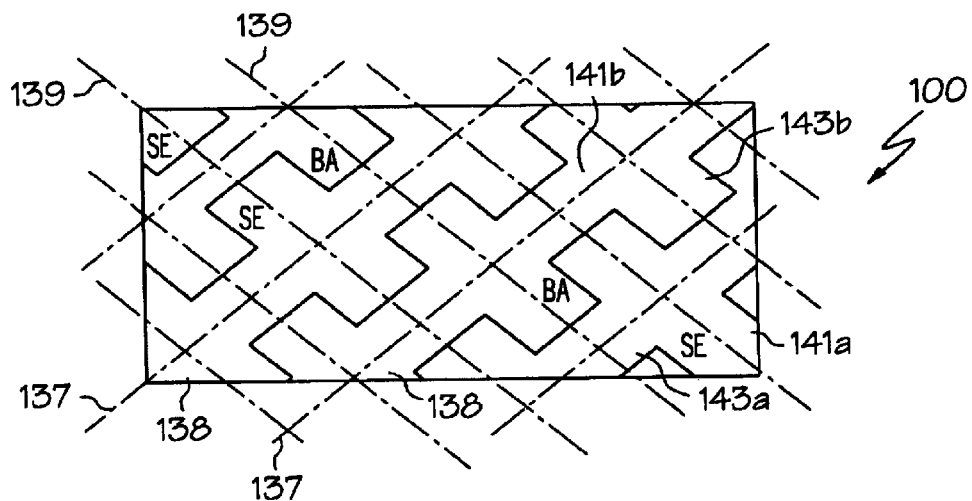
FIG. 6a shows an inventive stent in side elevational view with helical strips.

The invention is further directed to a stent, such as that shown at 100 in side elevational view in FIG. 6a, comprising a plurality of sections including at least one self-expanding section 136 which extends helically about the longitudinal axis of the stent and at least one balloon expandable but non-self-expanding section 138 which extends helically about the longitudinal axis of the stent. The helices are characterized by helical axis 137.

Typically, the stent will comprise a plurality of self-expanding sections and a plurality of balloon expandable but non-self-expanding sections. Optionally, as shown in FIG. 6a, the self-expanding section or sections also form a discontinuous pattern extending in a second helical direction about the longitudinal axis. Similarly, the balloon expandable but non-self-expanding sections form a discontinuous pattern extending helically about the longitudinal axis of the stent. The discontinuous helices are characterized by helical axis 139. The discontinuous helices are defined by the pattern of wide portions of the helical strips each helical strip 136 and 138 comprises a pattern of alternating narrow portions 141*a,b* and wide portions 143*a,b*.

Figure 6B:
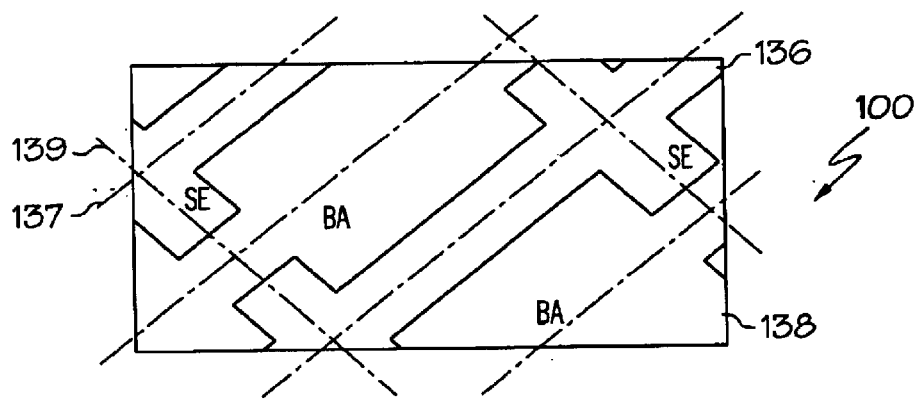
FIG. 6b shows another inventive stent in side elevational view with helical strips.

Another stent pattern within the scope of the invention is shown in FIG. 6b. In the stent pattern of FIG. 6b, the balloon expandable but non-self-expanding sections 138 predominate over the self-expanding sections 136. As shown in FIG. 6b, the balloon expandable sections account for more of the surface area of the stent and are wider than the self-expanding sections. In other embodiments of the invention, the self-expanding section(s) may account for more of the surface area of the stent than the balloon expandable section(s).

The stents of FIGS. 3–6 may be made in either left-handed or right handed helical embodiments.

The stents of FIGS. 3–6 may be made by starting with flat sheets of materials which are but welded together to form a stent preform. An appropriate stent pattern may be provided in the stent prefrom and the preform rolled into a tube. Optionally, the longitudinal edges of the stent may be joined together as by welding or any other suitable technique. The stents of FIGS. 3–6 may also be formed through a variety of other techniques. For example, the different strips may be formed of powdered metals or polymers which have been fused together. Examples of stents made from powdered metals and other materials and their methods of manufacture are disclosed in U.S. Pat. No. 5,972,027 and U.S. Pat. No. 5,843,172. The resulting stent preform may then be rolled. The stents of FIGS. 3–6 may also be made from powdered metals by forming a tube directly from powdered metals. Different powdered metals may be used for the self-expanding sections and for the balloon expandable sections with the tubular stent preform molded directly from powdered metals. An appropriate stent pattern may then be provided in the tubular stent preform.

In a most desirable embodiment of the invention, any of the above described embodiments are constructed and arranged such that balloon expansion of the stent is the controlling mechanism for initial expansion of the stent. The balloon expandable but non-self-expanding portions of the stent will prevent any significant expansion of the self-expanding portions of the stent. Once the stent is balloon expanded, additional expansion results from the self-expanding portions of the stent. This may be accomplished, for example, by distributing a few islands of self-expanding cells amongst a larger area of balloon expandable non-self-expanding cells with the overall structure of the stent being predominately balloon expandable.

Figure 7:
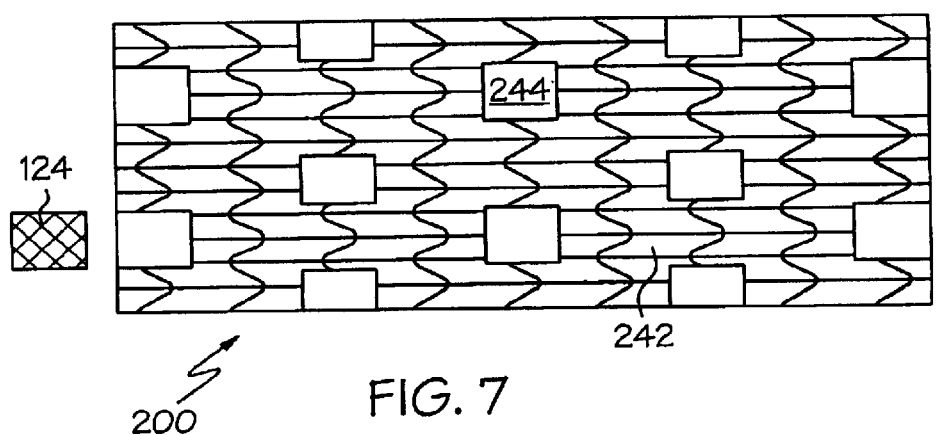
FIG. 7 shows a stent precursor for use in an inventive method of manufacturing a stent.

The invention is also directed to a method of manufacturing a stent. In accordance with the method, a tubular stent preform or a stent preform in the form of a sheet such as that shown by way of example at 200 in FIG. 7 is provided. Stent preform 200 is made of a non-self-expanding material having a plurality of first openings 242 therein corresponding to a desired stent pattern and at least one second opening 244 therein for receiving a self-expandable stent material therein. In accordance with the invention, a self-expandable segment such as that shown by way example at 124 is disposed in the second opening(s) and secured to the stent preform. Where the stent preform is in the form of a sheet, the method further comprises the steps of rolling the sheet to form a tube. An example of an inventive stent which may be made in accordance with the inventive method is shown at 100 in FIG. 2. Typically, as shown in FIG. 7, the stent preform has a plurality of second openings therein and a self-expandable segment is disposed in each second opening and secured to the stent preform.

In accordance with the invention, the stent preform may be made of stainless steel, desirably 316L, and the self-expandable segments are made of a shape memory alloy. Other suitable materials may also be used for the stent preform and for the self-expandable segments. Desirably, a shape memory stainless steel alloy will be used for the self-expanding segments. One suitable stainless steel shape memory alloy for use in the inventive stents is an FeMnSiCrNi shape memory stainless steel alloy. Another suitable self-expanding metal which may be used is nitinol. Shape memory polymers may also be used. The stent preform, or those portions corresponding to the balloon expandable but non-self-expanding portion of the resulting stent, may be made of other metals such as titanium, tantalum, gold or any other biocompatible metal or polymer which may be arranged in a balloon expandable configuration.

Any suitable technique may be used to secure the self-expandable segments to the stent preform. One such suitable method involves laser welding the self-expandable segments to the stent preform. Another suitable method involves using standard welding techniques to join the self-expanding and balloon expandable segments. Yet another method is via the use of adhesives.

The invention is further directed to a method of manufacturing a stent comprising the steps of providing a tube or a sheet, the tube or sheet made of a first metal and a second metal secured one to the other, optionally disposing an anti-galvanic coating thereon. Where a sheet is provided, the sheet is rolled into a tube. A paclitaxel/SIBS (styrene isobutylene styrene) compound is disposed on the anti-galvanic coating. Any suitable anti-galvanic coating may be used. Suitable anti-galvanic coatings include metallic coatings such as titanium and ceramic based coatings such as silicon dioxide. Where used, the anti-galvanic coating may be applied via any suitable technique including, by way of example, vapor deposition. It is believed that the anti-galvanic coating may prove useful by preventing any electrolyte from contacting the two dissimilar metals of the stent in order to prevent galvanic corrosion. Typically, the tube or sheet will have a pattern cut therein and the resulting stent will, optionally, be subjected to a suitable polishing process. A non-limiting example of a suitable polishing process is electropolishing.

Desirably, the stent pattern is cut into the sheet or tube and the sheet or tube is polished prior to disposing the anti-galvanic coating thereon. The anti-galvanic coating and paclitaxol/SIBS coating are then disposed on the tube or sheet.

The invention is also directed to a method of manufacturing a stent from a tube or a sheet, where the tube or the sheet is made from both pieces of shape memory alloy, and pieces of balloon-expandable but non-self-expanding alloy, for example type 316 stainless steel, arranged in regular helical patterns. Openings are provided in the tube or sheet via laser cutting, chemical etching or any other suitable technique to provide a cellular configuration. Desirably, the cells are only cut in each metal type.

In another embodiment of the invention, as shown in FIG. 6, a stent is provided which is formed of a plurality of left handed helices and a plurality of right handed helices. The right and left handed helices are arranged to cross over at several places. Cells are cut in each metal type but the cells desirably do not extend between adjacent metal types to avoid the possibility of having a significant number of individual cells crossing from one metal type to the other, and blurring the distinct effect of each.

It may also be advantageous to form these strips with stepped edges, with steps corresponding to the cell size, in an effort to enclose each cell more completely in its own metal type. It may also be useful to cut the non-shape memory effect metal strips twice the width of the SMA strips in order to provide for a double row helix, or several such helices, as a means of achieving a stent with a high proportion of balloon expandable cells.

The invention is further directed to a method of manufacturing a stent comprising the steps of disposing a tube on a mandrel. The tube comprises at least one section which is self-expanding and at least one section which is balloon expandable but non-self-expanding. The tube is then heat treated with the at least one self-expanding section expanded to a cross-section at least in excess, and desirably at least 10% in excess, of the maximum diameter of the balloon expandable but non-self-expanding section. This will allow the free region of the shape memory effect cells to expand or radially extend beyond the balloon expanded diameter in order to improve the security of the stent in the vessel and resist migration. The tube will typically contain a desired pattern of openings in the self-expanding section and in the balloon expandable section to facilitate expansion thereof.

The invention is also directed to a method of manufacturing a stent comprising the steps of providing a stent preform in the form of a tube or a sheet, the stent preform made of a first metal and a second metal secured one to the other, the first metal being a shape memory metal, the second metal being a non-shape memory metal, providing a plurality of openings in the first metal to provide a plurality of first cells in the first metal and providing a plurality of openings in the second metal to create a plurality of second cells in the second metal and, where the stent preform is in the form of a sheet, rolling the sheet into a tube. Because each of the cells is entirely cut within one of the types of metal, the resulting cells are either of the self-expanding type or balloon expandable, but not both. The adjacent portions of metal may be secured one to the other via any suitable technique including butt welding.

The invention is also directed to a stent comprising an FeMnSiCrNi shape memory stainless steel. Desirably, the stent further comprises a balloon expandable non-shape memory metal. Optionally, the entirety of the stent may be made of the FeMnSiCrNi shape memory stainless steel.

It is believed that the inventive stents will be of particular benefit in providing support to vessels which have been treated with therapeutic agents. Typically, as discussed above, following treatment of a vessel, balloon expandable stents tend to lose their tight fit in the vessel. The self-expanding sections of the inventive stents disclosed may hold the stent in place even as the vessel wall tends to pull away from the stent. To that end, the use of other coatings on the inventive stents is also within the scope of the invention.

The coating may comprise one or more non-genetic therapeutic agents, genetic materials and cells and combinations thereof as well as other polymeric coatings Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive stents disclosed herein may be of substantially uniform diameter or of non-uniform diameter. For example, the inventive stent may taper in the expanded state. This may be accomplished, for example, where the stent comprises serpentine bands, by decreasing the amplitude of the serpentine bands from one end of the stent to the other, or just along a desired portion of the stent. A tapered portion may be provided anywhere along the stent. For example, half of the stent, starting at one end of the stent, may be provided with a taper. Another way to achieve a tapered expanded stent is to change the stiffness of the serpentine bands and/or any connectors which extend between serpentine bands such that the stiffness of the serpentine bands and/or the connectors varies along the length of the stent. The stiffness of the various portions of the stent may be changed by altering length, width or thickness, adding additional stiffening material, using a chemical or mechanical means to alter the physical properties of the stent material, or applying one or a series of elastic elements about the stent.

The inventive stents may be used in arteries and vessels including coronary vasculature, the esophagus, the trachea, the colon, the biliary tract, the urinary tract, the prostate, the brain, urethras, fallopian tubes, and bronchial tubes.

Many of the inventive stents disclosed herein combine advantages of a balloon expandable stents with the advantages of a self-expanding stent with different regions of the stent exhibiting different properties. The degree to which the self-expanding and balloon expanding properties are present depends for each stent on the number of cells of each type present as well as on the spatial relationship between the various types of cells present in the stent. Stents having a large number of balloon expandable cells, for example, are likely to confer a high initial radial force on the walls of a vessel with the self-expanding cells compensating for any loosening of the stent which may occur over time.

Typically, the inventive stents will be delivered via a stent delivery catheter with an expandable member such as a balloon. Desirably, the catheter will include a deployment sheath disposed about the stent. Suitable catheters for use with the inventive stents are known in the art.

Although a self-expanding stent will typically interact with a deployment sheath which may possibly damage any coating on the stent, in some of the inventive embodiments disclosed herein, sufficient balloon-expandable but non-self-expanding sections may be provided to hold the self-expanding cells close to the crimped diameter of the stent and avoid frictional contact with the deployment sheath.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The particular features presented in the dependent claims can be combined with each other in other manners within the scope of the invention such that the invention should be recognized as also specifically directed to other embodiments having any other possible combination of the fratures of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the embodiments of the invention. Those skilled in the art may recognize other equivalents to the specific embodiment described herein which equivalents are intended to be encompassed by the claims attached hereto.

What is claimed is:

1. An unexpanded stent comprising a plurality of segments including:

a first balloon expandable segment which is not self-expanding, the first balloon expandable segment defining a plurality of balloon expandable cells therein;

a second balloon expandable segment which is not self-expanding, the second balloon expandable segment defining a plurality of balloon expandable cells therein; and a plurality of self-expanding segments, each self-expanding segment being non-abutting to any other self-expanding segment, some of the plurality of self-expanding segments being longitudinally and circumferentially offset from one another, each self-expanding segment defining a plurality of self-expanding cells therein, the self-expanding cells made of a shape memory material;

the stent having a distal-most end and a proximal-most end, each end constructed of balloon expandable material.

2. The stent of claim 1 wherein the self-expanding segments are regularly distributed about the stent.

3. The stent of claim 1 comprising more balloon expandable but non-self-expanding cells than self-expanding cells.

4. The stent of claim 1 wherein the stent has a protective covering.

5. The stent of claim 1 wherein at least 50% of the stent is made from one piece balloon expandable metal.

6. The stent of claim 1 wherein at least one self-expanding segment is located at an end of the stent.

7. The stent of claim 1 wherein the segments are irregularly shaped.

8. The stent of claim 1 wherein the balloon expandable segments are made of stainless steel and the self-expanding segments are made of a shape memory alloy.

9. The stent of claim 8 wherein the shape memory alloy is FeMnSiCrNi shape memory stainless steel.

* * * * *